(12) United States Patent
Bell et al.

(10) Patent No.: US 6,395,909 B1
(45) Date of Patent: May 28, 2002

(54) SUBSTITUTED BENZOPYRAN DERIVATIVES AND THEIR USE AS ANTICONVULSANTS

(76) Inventors: David Bell; Peter J. Cox; Mervyn Thompson; Gillian Turner, all of P.O. Box 1539, King of Prussia, PA (US) 19406-0939

( * ) Notice: Subject to any disclaimer, the term of this patent is extended or adjusted under 35 U.S.C. 154(b) by 0 days.

(21) Appl. No.: 09/720,019

(22) PCT Filed: Jun. 25, 1999

(86) PCT No.: PCT/GB99/02000

§ 371 (c)(1),
(2), (4) Date: Dec. 19, 2000

(87) PCT Pub. No.: WO00/00484

PCT Pub. Date: Jan. 6, 2000

(30) Foreign Application Priority Data

Jun. 29, 1998 (GB) .................................................. 9813949

(51) Int. Cl.$^7$ ............................................... C07D 311/04
(52) U.S. Cl. ........................ 549/404; 549/399; 549/405
(58) Field of Search ................................. 549/399, 404, 549/405

(56) References Cited

FOREIGN PATENT DOCUMENTS

| WO | WO92/22293 | * 12/1992 |
| WO | WO94/13656 | * 6/1994 |
| WO | WO94/13657 | * 6/1994 |
| WO | WO95/34545 | * 12/1995 |
| WO | WO95/34546 | * 12/1995 |
| WO | WO-95/34547 | * 12/1995 |

* cited by examiner

Primary Examiner—Ba K. Trinh

(57) ABSTRACT

This invention relates to 6-(hydroxyalkylcarbonyl) benzopyrans and their use as anticonvulsants.

11 Claims, No Drawings

SUBSTITUTED BENZOPYRAN DERIVATIVES AND THEIR USE AS ANTICONVULSANTS

This application is a 371 of PCT/GB99/02000 dated Jun. 25, 1999.

This invention relates to novel compounds, to processes for preparing them, and to their use as therapeutic agents.

EP-A-0 126 311, EP-A-0 376 524, EP-A-0 205 292, EP-A-0 250 077, EP-A-0 093 535, EP-A-0 150 202, EP-A-0 076 075 and WO/89/05808 (Beecham Group plc) describe certain benzopyran derivatives which possess anti-hypertensive activity.

EP-A-0 430 621 and EP-A-0 385 584 (Beecham Group plc) describe the resolution of certain intermediates useful in the preparation of the compounds described in the above mentioned patent applications.

EP-A-0 139 992 (Beecham Group plc) describes certain benzopyran derivatives which have cis isomerism at position 3 and 4 which compounds are described as possessing anti-hypertensive activity.

EP-A-0 587 645, EP-A-0 673 373, EP-A-0 673 374, EP-A-0 673 248, EP-A-0 674 519, WO95/34545, WO95/34547 and WO95/34546 (SmithKline Beecham plc) describe groups of benzopyran compounds possessing inter alia anti-convulsant activity.

This invention is based on the finding that further benzopyran compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, amyotrophic lateral sclerosis (ALS), ataxias, muscular rigidity (spasticity), and/or temporomandibular joint dysfunction.

Accordingly, the present invention provides a compound of formula (I) or pharmaceutically acceptable salt or solvate thereof:

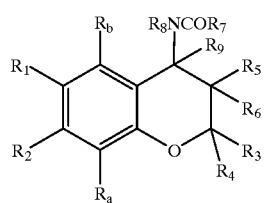

(I)

in which $R_1$ is $C_{1-6}$ alkylcarbonyl in which the alkyl group is substituted by OH;

$R_2$ is hydrogen or $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulfur, SO, $SO_2$, $CF_2$ or CFH; trifluoromethoxy, $C_{1-6}$ alkylsulfinyl, perfluoro $C_{2-6}$ alkylsulfonyl, $C_{1-6}$ alkylsulfonyl, $C_{1-6}$ alkoxysulfinyl, $C_{1-6}$ alkoxysulfonyl, aryl, heteroaryl, arylcarbonyl, heteroarylcarbonyl, phosphono, arylcarbonyloxy, heteroarylcarbonyloxy, arylsulfinyl, heteroarylsulfinyl, arylsulfonyl, heteroarylsulfonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulfinyl, aminosulfonyl or aminocarbonyl, any amino moiety being optionally substituted by one or two $C_{1-6}$ alkyl groups, or $C_{1-6}$ alkylsulfinylamino, $C_{1-6}$ alkylsulfonylamino, $C_{1-6}$ alkoxysulfinylamino or $C_{1-6}$ alkoxysulfonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, $R^a$ is hydrogen, halogen, nitro; $C_{1-4}$ alkylcarbonyl, $C_{1-4}$ alkyl; aryl $C_{1-4}$ alkyl, aryl $C_{1-4}$ alkenyl, heteroaryl $C_{1-4}$ alkyl or heteroaryl $C_{1-4}$ alkenyl, $R^b$ is hydrogen, halogen, nitro; $C_{1-4}$ alkylcarbonyl or $C_{1-4}$ alkyl; and in which any aryl or heteroaryl or alkyl moiety associated with $R^a$ or $R^b$ are optionally substituted;

one of $R_3$ and $R_4$ is hydrogen or $C_{1-4}$ alkyl and the other is $C_{1-4}$ alkyl, $CF_3$ or $CH_2X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl;

or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;

$R_7$ is heteroaryl or phenyl; both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; optionally substituted aryloxy or heteroaryloxy; $C_{1-4}$ alkoxy substituted by one or more halogens; amino substituted by $C_{1-4}$ alkanoyl, aroyl, aryl, phenylsulfonyl or $C_{1-4}$ alkylsulfonyl; $C_{1-4}$ alkyl substituted by one or more halogens or alkoxy; phenylsulfonyl $C_{1-4}$ alkyl sulfonyl, aminosulfonyl in which the amino group is optionally substituted by $C_{1-4}$ alkyl; $CONH_2$ in which the amino group is optionally substituted by $C_{1-4}$ alkyl;

$R_8$ is hydrogen; $C_{1-6}$ alkyl, $OR_{16}$ or $NHCOR_{17}$ wherein $R_{16}$ is hydrogen, $C_{1-6}$ alkyl, formyl, $C_{1-6}$ alkanoyl, aroyl or aryl-$C_{1-6}$ alkyl and $R_{17}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;

or $R_7$ and $R_8$ together form a $C_{3-4}$ alkylene group; and the $R_8$—N—CO—$R_7$ group is cis or trans to the $R_5$ group.

A preferred group of compounds are of formula (IA)

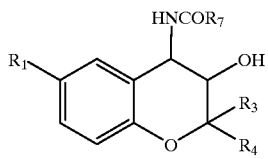

(IA)

i.e. $R_2$, $R_6$, $R_8$, $R_9$, $R_a$ and $R_b$ are hydrogen, $R_5$ is hydroxyl, $R_3$ and $R_4$ are both methyl, or one of $R_3$ and $R_4$ is methyl and the other of $R_3$ and $R_4$ is hydroxymethyl, and the $R_7$CONH group is cis or trans to the $R_5$ hydroxyl group.

Preferably $R_7$ is phenyl or heteroaryl which may be optionally substituted by up to three substituents independently selected from:

bromo, chloro, fluoro, iodo, nitro, amino optionally substituted once or twice by $C_{1-4}$ alkyl, cyano, azido, $C_{1-4}$ alkyl, $C_{1-4}$ alkoxy, trifluoromethyl or trifluoromethoxy.

More preferably $R_7$ is phenyl substituted by one or two groups independently selected from chlorine and fluorine.

It should be appreciated that the compounds of formula (I) may have chiral carbon atoms at positions 2, 3 or 4 and therefore may exist as enantiomers. The present invention extends to each enantiomer and to mixtures thereof including racemates. It should further be appreciated that particular enantiomeric forms are preferred for different utilities, thus for utilities other than sub-arachnoid haemorrhage or neural shock the 3R, 4S and 3S, 4S enantiomers are preferred, however, for sub-arachnoid haemorrhage or neural shock the 3S, 4R and 3R, 4R enantiomers are preferred.

The present invention further provides a compound of formula (I), or a pharmaceutically acceptable salt thereof as hereinbefore defined which exists predominantly in the cis 3S, 4S or trans 3R, 4S enantiomeric form.

The term "exists predominantly in the 3S, 4S enantiomeric form" means that there is greater than 50% of the 3S, 4S enantiomer present compared to the 3R, 4R enantiomer. More preferably there is greater than 60% of the 3S, 4S enantiomer present, yet more preferably greater than 70% of the 3S, 4S enantiomer present, even more preferably greater than 80% of the 3S, 4S enantiomer present and more preferably still greater than 90% of the 3S, 4S enantiomer present. Most preferably there is greater than 95% of the 3S, 4S enantiomer compound relative to the 3R, 4R enantiomer.

The term "exists predominantly in the 3R, 4S enantiomeric form" means that there is greater than 50% of the 3R, 4S enantiomer present compared to the 3S, 4R enantiomer. More preferably there is greater than 60% of the 3R, 4S enantiomer present, yet more preferably greater than 70% of the 3R, 4S enantiomer present, even more preferably greater than 80% of the 3R, 4S enantiomer present and more preferably still greater than 90% of the 3R, 4S enantiomer present. Most preferably there is greater than 95% of the 3R, 4S enantiomer compound relative to the 3S, 4R enantiomer.

Examples of compounds of formula (I) are:

(3R,4S)-4-(3,5-difluorobenzamido)-3,4-dihydro-2,2-dimethyl-3-hydroxy-6-(2-hydroxyacetyl)-2H-1-benzopyran (3S,4S)-4-(3-chloro-4-fluorobenzamido)-3,4-dihydro-2,2-dimethyl-3-hydroxy-6-(2-hydroxyacetyl)-2H-1-benzopyran (3R,4S)-4-(4-fluorobenzamido)-3,4-dihydro-2,2-dimethyl-3-hydroxy-6-(2-hydroxyacetyl)-2H-1-benzopyran When synthesised, these compounds may be isolated in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories.

Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction.

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction.

The present invention also provides a process for the preparation of compounds of formula (I), which comprises treating a compound of formula (II):

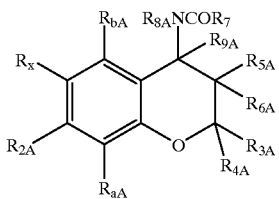

(II)

in which $R_x$ is a $C_{1-6}$alkyl carbonyl group, and $R_{2A}$, $R_{3A}$, $R_{4A}$, $R_{5A}$, $R_{6A}$, $R_{7A}$, $R_{8A}$, $R_{9A}$, $R_{aA}$ and $R_{bA}$ are $R_2$, $R_3$, $R_4$, $R_5$, $R_6$, $R_7$, $R_8$, $R_9$, $R_a$, and $R_b$ as defined for formula (I) or a group or groups convertible to $R_2$, $R_3$, $R_4$, $R_5$, $R_6$, $R_7$, $R_8$, $R_9$, $R_a$ and $R_b$, with a reagent or sequence of reagents which introduces a hydroxyl group into the alkyl group of $R_x$; and where required converting an $R_{2A}$, $R_{3A}$, $R_{4A}$, $R_{5A}$, $R_{6A}$, $R_{7A}$, $R_{8A}$, $R_{9A}$, $R_{aA}$ or $R_{bA}$ group to a $R_2$, $R_3$, $R_4$, $R_5$, $R_6$, $R_7$, $R_8$, $R_9$, $R_a$ or $R_b$ group, converting one $R_2$, $R_3$, $R_4$, $R_5$, $R_6$, $R_7$, $R_8$, $R_9$, $R_a$ or $R_b$ group to another $R_2$, $R_3$, $R_4$, $R_5$, $R_6$, $R_7$, $R_8$, $R_9$, $R_a$ or $R_b$ group, converting a salt product to the free base or another pharmaceutically acceptable salt, or converting a free base product to a pharmaceutically acceptable salt.

For example, the compounds of formula (II) may be reacted with [bis(trifluoroacetoxy)iodo]benzene, by heating under reflux in a suitable solvent.

Conversions of an $R_{2A}$, etc., group to an $R_2$, etc group typically arise when a protecting group is needed during the above reaction or during the preparation of the reactants by the procedures described below, or when it is easier to introduce a bulky or reactive substituent at the end of a synthetic sequence. Interconversion of one $R_2$, etc., group to another typically arises when one compound of formula (I) is used as the precursor of another compound of formula (I).

The group $R_1$, once formed, may also require protection with a protecting group during the conversion of $R_{2A}$ etc to $R_2$ etc and/or the conversion of one $R_2$ etc to another $R_2$ etc.

The preparation of compounds of formula (II) is described in the above referenced Beecham Group and SmithKline Beecham patent applications, with especial reference to EP-A-0766075, EP-A-0126311, WO 94/13656 and WO 95/34545.

More particularly, compounds of formula (II) may be prepared by reacting a compound of formula (III)

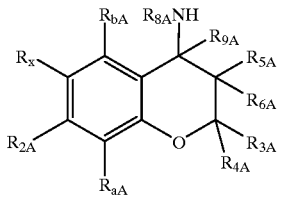

(III)

with a compound of formula (IV)

$R_{7A}CO.L$ (IV)

in which L is OH, acyloxy, or a halogen, especially Cl or Br, under conventional conditions for coupling carboxylic acids or active derivatives thereof with amines. For example, see the conditions for the similar coupling in Examples 2,5 and 6 in WO 94/13656.

As indicated previously, compounds of formula (I) may be in the trans or cis configuration as regards the position of the group $R_8NCOR_7$ relative to the group $R_5$, and the configuration of the compounds of formula (I) will follow from the configuration of the precursor of formula (II). Compounds of formula (II) may be prepared in the trans form using procedures which are generally described in EP-0126311, EP-0376524, EP-205292, EP-0250077, EP-0093535, EP-0150202, EP-0076075 and WO 89/05808.

The cis compounds may be prepared by procedures generally described in or analogous to those described in EP-A-0139992. Also cis compounds may be prepared from the corresponding trans compounds by the procedure described in WO 94/13657 when $R_5$ is hydroxy and $R_8$ is hydrogen, by treatment with trifluoromethane sulphonic anhydride to form an intermediate cis-oxazoline compound.

It should be appreciated that racemates of formula (I) or formula (II) may be resolved, or enantiomerically purified compounds of formula (I) or formula (II) may be prepared using procedures conventional in the art, and in particular using the procedures outlined in EP-A-0430631 and EP-A-0355584.

It is preferred that the compounds of formula (II) are prepared in the required enantiomeric form by forming a chirally pure epoxide using catalysts and conditions generally outlined in WO 91/14694 or WO 93/17026 and thereafter converting the epoxides to the required compound of formula (II) using procedures outlined herein.

Compounds of formula (III) may be prepared by treating a compound of formula (V)

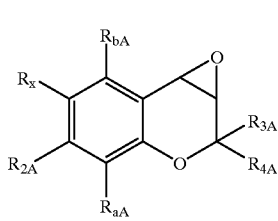

(V)

with ammonium hydroxide.

The epoxy compounds of formula (V) may be prepared as disclosed in EP-A-0076075 or GB-A-1511187, for example from compounds of formula (VI)

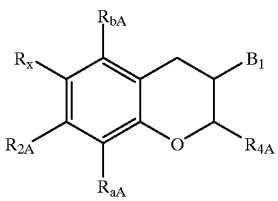

(VI)

Compounds of formula (VI) may be prepared as in GB-A-1511187 or using procedures analogous to those described therein.

Compounds of formula (IV) are commercially available carboxylic acids or acid halides or may be prepared by further substitution of commercially available compounds using conventional procedures or by oxidation of corresponding alcohols. For the preferred substituted phenyl compounds, substituted benzoic acids that are not readily available may be prepared by oxidation of corresponding substituted benzyl alcohols. Alternatively benzoic acids can be prepared from correpondingly substituted phenols, for example by formation of the acetate, conversion to an acetophenone and then to the desired acid.

The preparation of compounds of this invention is further illustrated by the following Descriptions and Examples. The utility of compounds of this invention is shown by the Pharmacological Data that follow the Examples.

Description 1

(3R,4S)-6-Acetyl-4-amino-3,4-dihydro-2,2-dimethyl-3-hydroxy-2H-1-benzopyran

From (3R,4S)-6-acetyl-3,4-epoxy-3,4-dihydro-2,2-dimethyl-2H-1-benzopyran (Example 1 of GB-A-1511187) by stirring in ethanolic ammonium hydroxide solution.

Description 2

(3S,4S)-6-Acetyl-4-amino-3,4-dihydro-2,2-dimethyl-3-hydroxy-2H-1-benzopyran

From D1 via oxazoline derivative using methods analagous to those disclosed in EP-A-0766075, EP-A-0126311, WO 94/13656 and WO 95/34545.

Description 3

(3R,4S)-6-Acetyl-4-(3,5-difluorobenzamido)-3,4-dihydro-2,2-dimethyl-3-hydroxy-2H-1-benzopyran From D1, reacting with 3,5-difluorobenzoyl chloride.

Description 4

(3S,4S)-6-Acetyl-4-(3-chloro-4-fluorobenzamido)-3,4-dihydro-2,2-dimethyl-3-hydroxy-2H-1-benzopyran From D2, reacting with 3-chloro-4-fluorobenzoyl chloride.

Description 5

(3R,4S)-6-Acetyl-4-(4-fluorobenzamido)-3,4-dihydro-2,2-dimethyl-3-hydroxy-2H-1-benzopyran From D1, reacting with 4-fluorobenzoyl chloride.

EXAMPLE 1

(3R,4S)-4-(3,5-difluorobenzamido)-3,4-dihydro-2,2-dimethyl-3-hydroxy-6-(2-hydroxyacetyl)-2H-1-benzopyran (3R,4S)-6-Acetyl-4-(3,5-difluorobenzamido)-3,4-dihydro-2,2-dimethyl-3-hydroxy-2H-1-benzopyran D3 (1.88 g, 5.0 mmol) (Example 4 of WO95/34545) was dissolved in acetonitrile (25ml), water (5 ml) and trifluoroacetic acid (0.77 ml, 10.0 mmol). [Bis(trifluoroacetoxy)iodo]benzene (4.30 g, 10.0 mmol) was added and the reaction stirred under reflux for three hours. The reaction mixture was allowed to cool and the acetonitrile was removed in vacuo, the resulting material being partitioned between water (50 ml) and dichloromethane (125 ml). The aqueous layer was extracted with further portions of dichloromethane (3×25 ml) and the combined organic extracts were dried over magnesium sulphate, filtered and the solvent removed in vacuo. The resulting yellow solid was purified by column chromatography on silica, eluting with 20% to 40% ethyl acetate in hexane to afford the title compound as a white solid (0.70 g, 36%, m.p. 179.4° C.).

$^1$H n.m.r. (DMSO):d 1.22 (s,3H,CH$_3$), 1.45 (s,3H,CH$_3$), 3.76 (m,1H,CH), 4.64 (m,2H,CH$_2$), 4.93 (t,1H,OH), 5.07 (m,1H,CH), 5.77 (d,1H,OH), 6.89 (d,1H,Ar), 7.50 (m,1H, Ar), 7.66 (m,3H,Ar), 7.75 (d,1H,Ar), 8.94 (d,1H,NH).

$^{13}$C n.m.r. (DMSO):d 18.8 (CH$_3$), 26.8 (CH$_3$), 49.9 (CHNH), 65.0 (CH$_2$), 71.3 (CHOH), 80.0 (C(CH$_3$)$_2$), 106.9 (t, J$_{CCF}$ 26 Hz, Ar), 110.9 (dd, J$_{CCF}$ 19 Hz, J$_{CCCCF}$ 7 Hz, 2×Ar), 116.8 (Ar), 123.6 (Ar), 127.6 (Ar), 128.1 (Ar), 128.9 (Ar), 138.0 (t, J$_{CCCF}$ 9 Hz, Ar), 156.9 (Ar), 162.4 (dd, J$_{CF}$ 246 Hz, J$_{CCCF}$ 13 Hz, 2×Ar), 164.8 (CONH), 197.3 (C=O).

FAB-MS m/e 392 (MH$^+$)

EXAMPLE 2

(3S,4S)-4-(3-chloro-4-fluorobenzamido)-3,4-dihydro-2,2-dimethyl-3-hydroxy-6-(2-hydroxyacetyl)-2H-1-benzopyran (3S,4S)-6-Acetyl-4-(3-chloro-4-fluorobenzamido)-3,4-dihydro-2,2-dimethyl-3-hydroxy-2H-1-benzopyran D4 (1.97 g, 5.0 mmol) (Example 17 of WO95/34545) was dissolved in acetonitrile (25 ml), water (5 ml) and trifluoroacetic acid (0.77 ml, 10.0 mmol). [Bis(trifluoroacetoxy)iodo]benzene (4.30 g, 10.0 mmol) was added and the reaction stirred under reflux for three hours. The reaction mixture was allowed to cool and the acetonitrile was removed in vacuo giving a yellow solid which was isolated by filtration and recrystallised from ethyl acetate/hexane to give the title compound as a white solid (0.48 g, 24%), m.p. 200° C.

$^1$H n.m.r. (DMSO):d 1.31 (s,3H,CH$_3$), 1.44 (s,3H,CH$_3$), 3.75 (m,1H,CH), 4.69 (d,2H,CH$_2$), 4.91 (t,1H,OH), 5.49 (m,1H,CH), 5.66 (d,1H,OH), 6.85 (d,1H,Ar), 7.56 (t,1H,Ar), 7.76 (m,1H,Ar), 7.79 (s,1H,Ar), 8.05 (m,1H,Ar), 8.28 (m,1H,Ar), 8.73 (d, 1H,NH).

$^{13}$C n.m.r. (DMSO):d 24.1 (CH$_3$), 25.1 (CH$_3$), 46.8 (CHNH), 64.9 (CH$_2$), 67.7 (CHOH), 79.2 (C(CH$_3$)$_2$), 116.4 (Ar), 116.9 (d, J$_{CCF}$ 21 Hz, Ar), 119.6 (d, J$_{CCF}$ 18 Hz, Ar), 120.6 (Ar), 126.9 (Ar), 128.6 (d, J$_{CCCF}$ 25 Hz, Ar), 129.2 (d, J$_{CCCF}$ 8 Hz, Ar), 130.5 (2×Ar), 131.9 (d, J$_{CCCCF}$ 4 Hz, Ar) 157.9 (Ar), 159.1 (d, J$_{CF}$ 249 Hz, Ar), 165.0 (CONH), 197.6 (CO).

CI$^+$ MS m/e 408 (MH$^+$)

EXAMPLE 3

Preparation of (3R,4S)-4-(4-fluorobenzamido)-3,4-dihydro-2,2-dimethyl-3-hydroxy-6-(2-hydroxyacetyl)-2H-1-benzopyran (3R,4S)-6-Acetyl-4-(4-fluorobenzamido)-3,4-dihydro-2,2-dimethyl-3-hydroxy-2H-1-benzopyran D5 (1.83 g, 5.0 mmol) (Example 20 of WO92/22293) was dissolved in acetonitrile (25 ml), water (5 ml) and trifluoroacetic acid (0.77 ml, 10.0 mmol). [Bis(trifluoroacetoxy)iodo]benzene (4.30 g, 10.0 mmol) was added and the reaction stirred under reflux for three hours. The reaction mixture was allowed to cool and the acetonitrile was removed in vacuo, the resulting material being partitioned between water (50 ml) and dichloromethane (125 ml). The aqueous layer was extracted with further portions of dichloromethane (3×25 ml) and the combined organic extracts were dried over magnesium sulphate, filtered and the solvent removed in vacuo. The resulting yellow foam was purified by column chromatography on silica, eluting with 20% to 50% ethyl acetate in hexane to afford the title compound as a white solid (0.44 g, 24%), m.p. 216° C.

$^1$H n.m.r. (DMSO):d 1.22 (s, 3H, CH$_3$), 1.45 (s, 3H, CH$_3$), 3.78 (m, 1H, CH), 4.63 (d, 2H, CH$_2$), 4.92 (t, 1H, OH), 5.09 (m, 1H, CH), 5.70 (d, 1H, OH), 6.88 (d, 1H, Ar), 7.35 (m, 2H, Ar), 7.70 (s, 1H, Ar), 7.76 (d, 1H, Ar), 8.02 (m, 2H, Ar), 8.81 (d,1H, NH).

$^{13}$C n.m.r. (DMSO):d 18.6 (CH$_3$), 26.7 (CH$_3$), 49.5 (CHNH), 64.8 (CH$_2$), 71.1 (CHOH), 79.9 (C(CH$_3$)$_2$), 115.1

(d, $J_{CCF}$ 21 Hz, 2×Ar), 116.6 (Ar), 123.9 (Ar), 127.3 (Ar), 128.0 (Ar), 128.7 (Ar), 130.0 (d, $J_{CCCF}$ 9 Hz, 2×Ar), 130.8 (d, $J_{CCCCF}$ 3 Hz, Ar), 156.8 (Ar), 163.9 (d, $J_{CF}$ 247 Hz, Ar), 166.1 (CONH), 197.5 (CO).

FAB-MS m/e 374 (MH$^+$)

Pharmacological Data

1. Binding Assay Method

WO 92/22293 (SmithKline Beecham) discloses compounds having anti-convulsant activity, including inter alia the compound (3R, 4S)-6-acetyl-(4-fluorobenzoylamino)-3,4-dihydro-2,2-dimethyl-2H-1-benzopyran-3-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test with pKi values greater than 6. For example, the compound of Example 1 had a pKi value of 7.35

2. MEST Test

The maximal electroshock seizure threshold (MEST) test in rodents is particularly sensitive for detecting potential anticonvulsant properties[1.] In this model, anticonvulsant agents elevate the threshold to electrically-induced seizures whilst proconvulsants lower the seizure threshold.

Method

Rats (naive male, Charles River, U.K. Sprague Dawley strain, 100–150 g) are randomly assigned to groups of 10–20 and dosed orally, intravenously or intraperitoneally at a dose volume of 1 ml/kg with various doses of compound (0.1–300 mg/kg) or vehicle. Rats are then subjected at 15 or 360 min post dose to a single electroshock (0.3 sec, 50 Hz, sine wave form) administered via corneal electrodes. The mean current and standard error required to induce a tonic seizure in 50% (CC$_{50}$) of the rats in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the CC$_{50}$ is usually 20–30 mA. Hence the first animal in the control group is subjected to a current of 25 mA. If a tonic seizure does not ensue, the current is increased for a subsequent rat. If a tonic convulsion does occur, then the current is decreased, and so on until all the animals in the group have been tested.

The percentage increase or decrease in CC$_{50}$ for each group compared to the control is calculated.

Studies are carried out using a Hugo Sachs Electronik Constant Current Shock Generator with totally variable control of shock level from 0 to 300 mA and steps of 5–20 mA are usually used. Drugs are suspended in 1% methyl cellulose or dissolved in appropriate vehicles.

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113

Results

Compounds of this invention dosed by the intravenous route as a solution in 20% PEG and tested 15–360 min post dosing show an increase in seizure threshold indicative of an anticonvulsant effect. For example, the compound of Example 1 dosed at 1 mg/kg and tested 30 min post dosing showed an increase in seizure threshold relative to control of 317%.

What is claimed is:

1. A compound of formula (I) or pharmaceutically acceptable salt or solvate thereof:

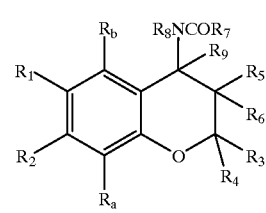

(I)

in which $R_1$ is $C_{1-6}$ alkylcarbonyl in which the alkyl group is substituted by OH;

$R_2$ is hydrogen or $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, CF$_3$S, or a group CF$_3$—A—, where A is —CF$_2$—, —CO—, —CH$_2$—, CH(OH), SO$_2$, SO, CH$_2$—O, or CONH, or a group CF$_2$H—A'— where A' is oxygen, sulfur, SO, SO$_2$, CF$_2$ or CFH; trifluoromethoxy, $C_{1-6}$ alkylsulfinyl, perfluoro $C_{2-6}$ alkylsulfonyl, $C_{1-6}$ alkylsulfonyl, $C_{1-6}$ alkoxysulfinyl, $C_{1-6}$ alkoxysulfonyl, aryl, heteroaryl, arylcarbonyl, heteroarylcarbonyl, phosphono, arylcarbonyloxy, heteroarylcarbonyloxy, arylsulfinyl, heteroarylsulfinyl, arylsulfonyl, heteroarylsulfonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulfinyl, aminosulfonyl or aminocarbonyl, any amino moiety being optionally substituted by one or two $C_{1-6}$ alkyl groups, or $C_{1-6}$ alkylsulfinylamino, $C_{1-6}$ alkylsulfonylamino, $C_{1-6}$ alkoxysulfinylamino or $C_{1-6}$ alkoxysulfonylamino, or ethylenyl terminally substituted by $C_{1-6}$ alkylcarbonyl, nitro or cyano, or —C($C_{1-6}$ alkyl)NOH or —C($C_{1-6}$ alkyl)$NNH_2$, $R^a$ is hydrogen, halogen, nitro; $C_{1-4}$ alkylcarbonyl, $C_{1-4}$ alkyl; aryl $C_{1-4}$ alkyl, aryl $C_{1-4}$ alkenyl, heteroaryl $C_{1-4}$ alkyl or heteroaryl $C_{1-4}$ alkenyl, $R^b$ is hydrogen, halogen, nitro; $C_{1-4}$ alkylcarbonyl or $C_{1-4}$ alkyl; and in which any aryl or heteroaryl or alkyl moiety associated with $R^a$ or $R^b$ are optionally substituted;

one of $R_3$ and $R_4$ is hydrogen or $C_{1-4}$ alkyl and the other is $C_{1-4}$ alkyl, $CF_3$ or $CH_2X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;

$R_7$ is heteroaryl or phenyl; both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; optionally substituted aryloxy or heteroaryloxy; $C_{1-4}$ alkoxy substituted by one or more halogens; amino substituted by $C_{1-4}$ alkanoyl, aroyl, aryl, phenylsulfonyl or $C_{1-4}$ alkylsulfonyl; $C_{1-4}$ alkyl substituted by one or more halogens or alkoxy; phenylsulfonyl $C_{1-4}$ alkyl sulfonyl, aminosulfonyl in which the amino group is optionally substituted by $C_{1-4}$ alkyl; $CONH_2$ in which the amino group is optionally substituted by $C_{1-4}$ alkyl;

$R_8$ is hydrogen; $C_{1-6}$ alkyl, $OR_{16}$ or $NHCOR_{17}$ wherein $R_{16}$ is hydrogen, $C_{1-6}$ alkyl, formyl, $C_{1-6}$ alkanoyl, aroyl or aryl-$C_{1-6}$ alkyl and $R_{17}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;

or $R_7$ and $R_8$ together form a $C_{3-4}$ alkylene group;
and the $R_8$—N—CO—$R_7$ group is cis or trans to the $R_5$ group.

2. A compound of formula (I) according to claim 1, or a pharmaceutically acceptable salt thereof, which exists predominantly in the cis 3S, 4S or trans 3R, 4S enantiomeric form.

3. A compound of formula (I) according to claim 2 wherein there is greater than 60% of the 3S, 4S enantiomer present compared to the 3R, 4R enantiomer.

4. A compound of formula (I) according to claim 2 wherein there is greater than 60% of the 3R, 4S enantiomer present compared to the 3S, 4R enantiomer.

5. A compound according to claim 1 which is of formula (IA)

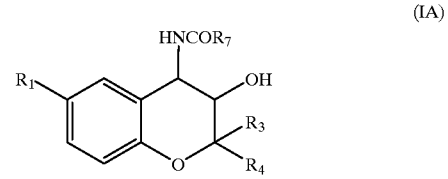

(IA)

wherein:
$R_3$ and $R_4$ are both methyl, or one of $R_3$ and $R_4$ is methyl and the other of $R_3$ and $R_4$ is hydroxymethyl, and the $R_7$CONH group is cis or trans to the hydroxyl group.

6. A compound according to claim 1 wherein $R_7$ is phenyl or heteroaryl which may be optionally substituted by up to three substituents independently selected from:
bromo, chloro, fluoro, iodo, nitro, amino unsubstituted or substituted by one or two $C_{1-4}$ alkyl, cyano, azido, $C_{1-4}$ alkyl, $C_{1-4}$ alkoxy, trifluoromethyl or trifluoromethoxy groups.

7. A compound according to claim 6 wherein $R_7$ is phenyl substituted by one or two groups independently selected from chlorine and fluorine.

8. A compound according to claim 1 which is:
(3S,4S)-4-(3-chloro-4-fluorobenzamido)-3,4-dihydro-2,2-dimethyl-3-hydroxy-6-(2-hydroxyacetyl)-2H-1-benzopyran.

9. A compound according to claim 1 which is:

(3R,4S)-4-(3,5-difluorobenzamido)-3,4-dihydro-2,2-dimethyl-3-hydroxy-6-(2-hydroxyacetyl)-2H-1-benzopyran; and (3R,4S)-4-(4-fluorobenzamido)-3,4-dihydro-2,2-dimethyl-3-hydroxy-6-(2-hydroxyacetyl)-2H-1-benzopyran.

10. A pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, which comprises a compound of formula (I) according to claim 1 or a pharmaceutically acceptable salt or solvate thereof, and a pharmaceutically acceptable carrier.

11. A method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, comprising administering to the sufferer in need thereof an effective or prophylactic amount of a compound of formula (I) according to claim 1, or a pharmaceutically acceptable salt or solvate thereof.

* * * * *